(12) United States Patent
Hori et al.

(10) Patent No.: US 12,426,146 B2
(45) Date of Patent: Sep. 23, 2025

(54) ACCELERATOR AND PARTICLE THERAPY SYSTEM

(71) Applicant: Hitachi High-Tech Corporation, Tokyo (JP)

(72) Inventors: Chishin Hori, Tokyo (JP); Takamitsu Hae, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 398 days.

(21) Appl. No.: 18/031,162

(22) PCT Filed: Aug. 6, 2021

(86) PCT No.: PCT/JP2021/029368
§ 371 (c)(1),
(2) Date: Apr. 11, 2023

(87) PCT Pub. No.: WO2022/085273
PCT Pub. Date: Apr. 28, 2022

(65) Prior Publication Data
US 2023/0389169 A1 Nov. 30, 2023

(30) Foreign Application Priority Data

Oct. 21, 2020 (JP) ................................. 2020-176615

(51) Int. Cl.
*A61N 5/10* (2006.01)
*H05H 7/02* (2006.01)
(Continued)

(52) U.S. Cl.
CPC ................ *H05H 7/10* (2013.01); *H05H 7/02* (2013.01); *H05H 7/04* (2013.01); *H05H 13/02* (2013.01);
(Continued)

(58) Field of Classification Search
CPC .. H05H 7/10; H05H 7/02; H05H 7/04; H05H 13/02; H05H 2007/025; H05H 2277/11; A61N 5/1077; A61N 2005/1087
See application file for complete search history.

(56) References Cited

U.S. PATENT DOCUMENTS

| 5,410,558 A * | 4/1995 | Hackett .................... H05H 7/04 505/180 |
| 2019/0239334 A1 | 8/2019 | Aoki et al. |
| 2021/0195725 A1 | 6/2021 | Hae et al. |

FOREIGN PATENT DOCUMENTS

| JP | 2019-096404 A | 6/2019 |
| JP | 2019-133745 A | 8/2019 |

(Continued)

OTHER PUBLICATIONS

Extended European Search Report received in corresponding European Application No. 21882414.2 dated Sep. 19, 2024.
(Continued)

*Primary Examiner* — Kiho Kim
(74) *Attorney, Agent, or Firm* — MATTINGLY & MALUR, PC

(57) ABSTRACT

An object of the present invention is to speed up an operation of extracting an ion beam from an accelerator. An accelerator 100 includes an upper magnetic pole 8 and a lower magnetic pole 9 sandwiching an ion circulation space 10 in which ions circulate. At least one of the upper magnetic pole 8 and the lower magnetic pole 9 is formed such that a magnetic pole interval between the upper magnetic pole 8 and the lower magnetic pole 9 varies when the ion circulation space 10 is viewed along an ion beam trajectory. That is, a wide interval region 11 having a larger magnetic pole interval than a peripheral region is formed in a region closer
(Continued)

to a center point of the ion circulation space 10 than a center point of the ion beam trajectory.

14 Claims, 9 Drawing Sheets

(51) Int. Cl.
*H05H 7/04* (2006.01)
*H05H 7/10* (2006.01)
*H05H 13/02* (2006.01)

(52) U.S. Cl.
CPC .... *A61N 5/1077* (2013.01); *A61N 2005/1087* (2013.01); *H05H 2007/025* (2013.01); *H05H 2277/11* (2013.01)

(56) References Cited

FOREIGN PATENT DOCUMENTS

| | | | |
|---|---|---|---|
| JP | 2020-035728 W | 3/2020 | |
| JP | 2020-170688 A | 10/2020 | |
| JP | 6768845 B2 | 10/2020 | |

OTHER PUBLICATIONS

International Search Report of PCT/JP2021/029368 dated Oct. 12, 2021.

\* cited by examiner

ACCELERATOR AND PARTICLE THERAPY SYSTEM

TECHNICAL FIELD

The present invention relates to an accelerator and a particle therapy system, and more particularly to a technique for extracting an ion beam from the accelerator.

BACKGROUND ART

Particle therapy in which a target volume is irradiated with a particle beam is widely performed. In general, a particle therapy system including an accelerator is used in particle therapy. Ions such as carbon ions, helium ions, and protons are injected into the accelerator, and the ions are accelerated until the ions have energy necessary for treatment. A beam by the ions accelerated by the accelerator is irradiated toward the target volume. In the particle therapy system, the energy and spatial spread of the ion beam are adjusted in accordance with a position and shape of the target volume.

As a literature related to the particle therapy system, there is the following PTL 1. PTL 1 discloses a method of "extracting a charged particle beam by feeding a radio frequency different from a radio frequency used for acceleration to a charged particle beam" as a method for, "in a circular accelerator that feeds a radio frequency in a main magnetic field to accelerate a charged particle beam while increasing a trajectory radius, controlling extraction of the charged particle beam from the circular accelerator with high accuracy and improving a dose rate". Furthermore, an Example in which "beam energy can be arbitrarily changed between 70 MeV and 235 MeV to be emitted from the accelerator" is disclosed.

CITATION LIST

Patent Literature

PTL 1: JP 2019-133745 A
PTL 2: JP 2019-96404 A

SUMMARY OF INVENTION

Technical Problem

The accelerator disclosed in PTL 1 has a structure in which trajectories of ion beams (beam trajectories) are cotangential. Due to the cotangential trajectory structure, an aggregation region in which an interval between beam trajectories having different energies is narrowed is generated in the accelerator. In the aggregation region, electrodes of a radio frequency kicker are disposed so as to sandwich the beam trajectory included in an energy range to be extracted. When a radio frequency voltage is applied to the radio frequency kicker, a betatron oscillation amplitude of the ion beam passing through the region sandwiched between the electrodes of the radio frequency kicker is increased. Then, the ion beam having the increased betatron oscillation amplitude reaches a peeler magnetic field region or a regenerator magnetic field region disposed in a region on a radially outer side of a maximum energy trajectory, and receives the action of the peeler magnetic field region or the regenerator magnetic field region, whereby the ion beam is extracted to the outside of the accelerator.

In such an accelerator, among the ion beams extracted within a certain energy range, an ion beam having a relatively smaller energy has a smaller radius of the beam trajectory, and is away from the peeler magnetic field region and the regenerator magnetic field region. Therefore, the betatron oscillation amplitude required to extract the ion beam is large. Therefore, when the ion beam is extracted outside the accelerator, the response time from when the radio frequency voltage is applied to the radio frequency kicker to when the ion beam is extracted becomes longer as the energy of the ion beam is smaller.

An object of the present invention is to speed up an operation of extracting an ion beam from an accelerator.

Solution to Problem

An accelerator according to the present invention includes an upper magnetic pole and a lower magnetic pole sandwiching an ion circulation space in which ions circulate, in which the accelerator is configured such that there are spatial magnetic field variations when the ion circulation space is viewed along an ion beam trajectory, and the magnetic field variations are spatial magnetic field variations that displace ions such that an amount of displacement in an outward direction at an ion extraction operating point is larger for ions having smaller energy.

Furthermore, an accelerator according to the present invention includes an upper magnetic pole and a lower magnetic pole sandwiching an ion circulation space in which ions circulate, in which the accelerator is configured such that there are spatial magnetic field variations when the ion circulation space is viewed along an ion beam trajectory, and a magnetic field evaluation value along the ion beam trajectory in a region closer to a center point of the ion circulation space than to a center point of the ion beam trajectory is smaller than a magnetic field evaluation value along the ion beam trajectory in a region closer to an ion extraction operating point than to the center point of the ion beam trajectory.

Furthermore, an accelerator according to the present invention includes an upper magnetic pole and a lower magnetic pole sandwiching an ion circulation space in which ions circulate, in which at least one of the upper magnetic pole and the lower magnetic pole is formed such that a magnetic pole interval between the upper magnetic pole and the lower magnetic pole varies when the ion circulation space is viewed along an ion beam trajectory.

Advantageous Effects of Invention

According to the present invention, an operation of extracting an ion beam from an accelerator becomes fast.

DESCRIPTION OF EMBODIMENTS

Embodiments of the present invention will be described below with reference to the drawings. The same reference signs are given to the same matters illustrated in a plurality of the drawings, and duplicate description is avoided. Furthermore, terms representing shapes such as "circle" and "cylinder" in the present specification do not indicate only geometrically strictly defined shapes. The term representing the shape in the present specification also indicates a shape to which deformation is applied within a range in which the function of the component can be secured. Furthermore, terms such as "horizontal", "upper", and "lower" in the present specification are for convenience of description, and do not limit an attitude in a case where an accelerator is installed.

First Embodiment

Figure 1:
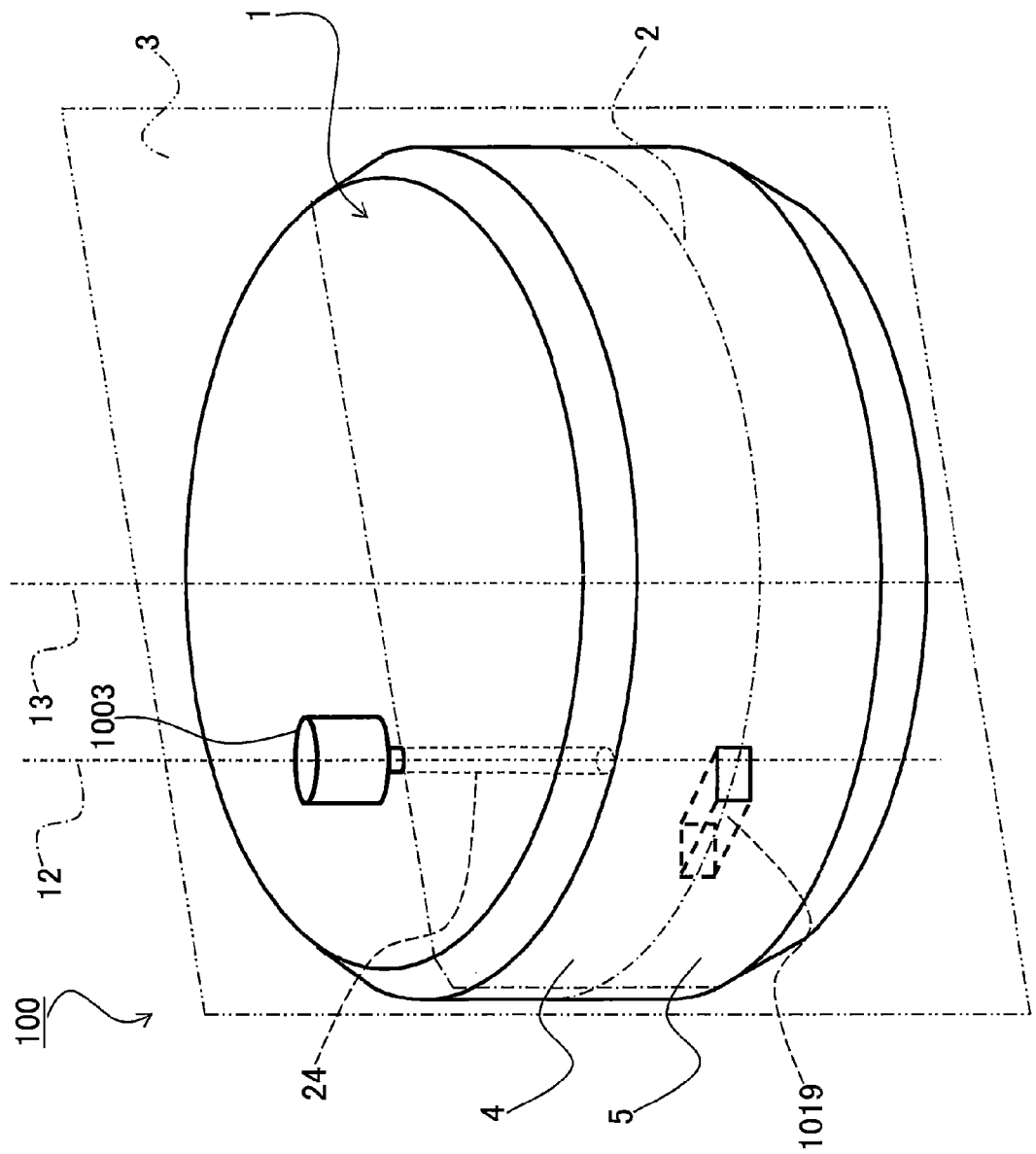
FIG. 1 is a perspective view of an accelerator.

FIG. 1 is a perspective view of an accelerator 100 according to a first embodiment of the present invention. Ions accelerated by the accelerator 100 may be hydrogen ions, that is, protons. When the protons are accelerated, the energy of an ion beam extracted from the accelerator 100 is, for example, 70 MeV or more and 225 MeV or less.

The accelerator 100 includes a main magnetic field magnet 1. The main magnetic field magnet 1 includes an upper return yoke 4 and a lower return yoke 5 that are circular when viewed from a vertical direction. The upper return yoke 4 is formed in a cylindrical container shape including a disk-shaped ceiling plate and side walls provided around the ceiling plate. The lower return yoke 5 is formed in a cylindrical container shape including a disk-shaped bottom plate and side walls provided around the bottom plate.

The upper return yoke 4 and the lower return yoke 5 are joined such that their respective openings are aligned. On a reference plane 2, which is a plane where the upper return yoke 4 and the lower return yoke 5 are joined, the ion beam being accelerated circulates. The upper return yoke 4 and the lower return yoke 5 may have a shape that is plane-symmetrical with respect to a vertical plane 3 that passes through a magnetic pole central axis 13 that is a central axis of the main magnetic field magnet 1, and is perpendicular to the reference plane 2. In FIG. 1, a line in which the reference plane 2 intersects the main field magnet 1 and a line in which the vertical plane 3 intersects the main field magnet 1 are indicated by one-dot chain lines.

An ion source 1003 is installed on an upper side of the main magnetic field magnet 1, and the upper return yoke 4 is provided with a through hole 24 into which ions are incident. The ion source 1003 may be installed inside the main magnetic field magnet 1.

Figure 2:
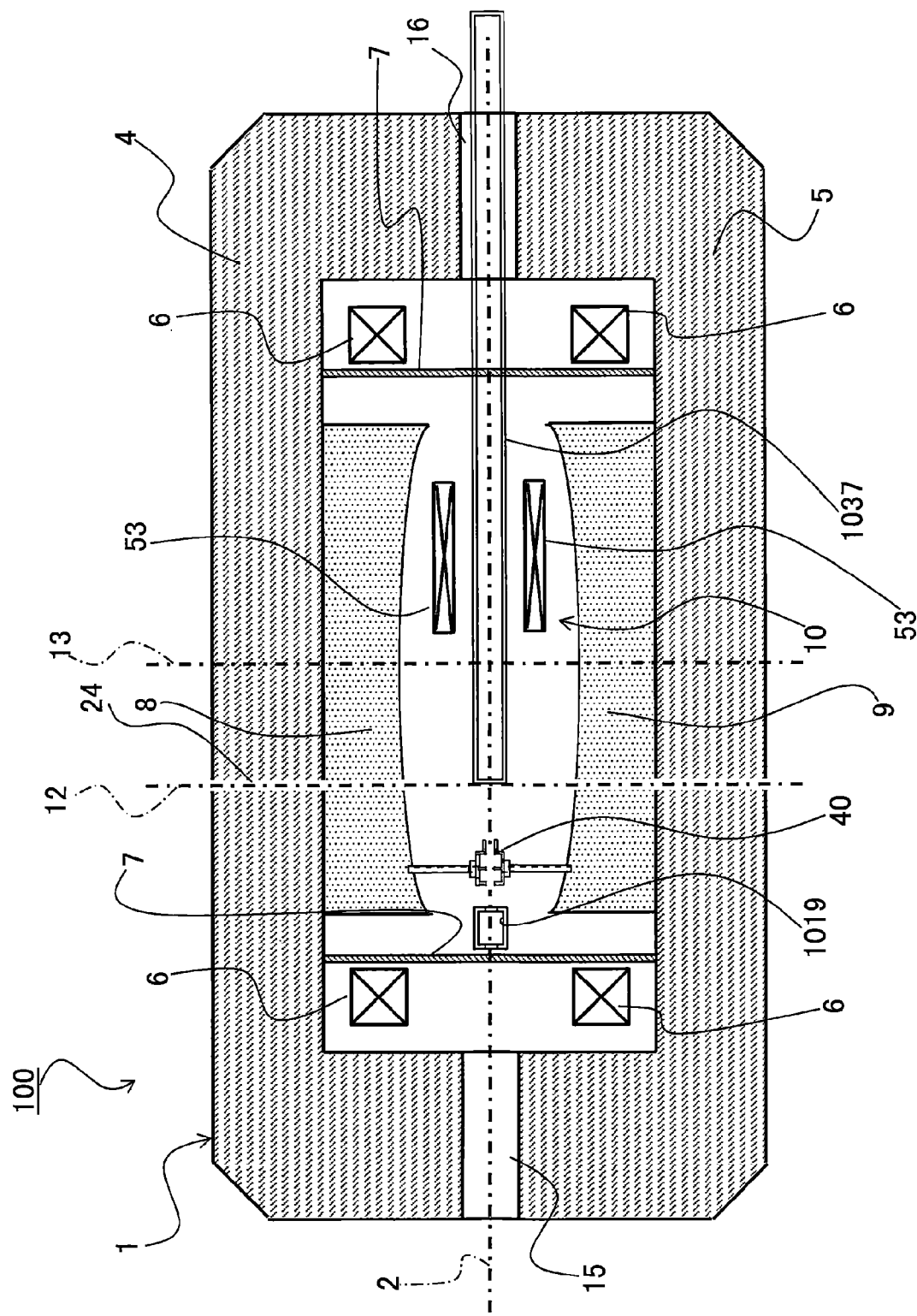
FIG. 2 is a view illustrating a cross section appearing when the accelerator is cut along a vertical plane.

FIG. 2 illustrates a cross section appearing when the accelerator 100 is cut along the vertical plane 3. As illustrated in FIG. 2, a pair of coils 6 is disposed in a space surrounded by the upper return yoke 4 and the lower return yoke 5 in plane symmetry with respect to the reference plane 2. Each of the coil 6 is connected to a coil excitation power supply provided outside the accelerator 100. The coil excitation power supply causes a current to flow in the coil 6.

The coil 6 is a superconducting coil and is installed inside a cryostat (not illustrated). The coil 6 is cooled by a refrigerant such as liquid helium or a refrigerator (not illustrated) in the cryostat.

A vacuum container 7 is provided inside the coil 6 in a space surrounded by the upper return yoke 4 and the lower return yoke 5. Inside the vacuum container 7, an upper magnetic pole 8 and a lower magnetic pole 9 are disposed so as to face each other vertically. That is, the upper magnetic pole 8 is disposed on a lower surface of the upper return yoke 4, and the lower magnetic pole 9 is disposed on an upper surface of the lower return yoke 5. An ion circulation space 10 that circulates and accelerates the ion beam is formed between the upper magnetic pole 8 and the lower magnetic pole 9.

The upper return yoke 4, the lower return yoke 5, the upper magnetic pole 8, and the lower magnetic pole 9 are made of, for example, pure iron with a reduced impurity concentration, low carbon steel, or the like. The vacuum container 7 is made of, for example, stainless steel. The coil 6 is made of, for example, a superconducting wire material using a superconductor such as niobium titanium.

An extraction channel 1019 includes an electromagnet, and the electromagnet is connected to a power supply for the extraction channel via a through hole 15. By causing a current to flow from the power supply for the extraction channel to the electromagnet provided in the extraction channel 1019, the ion beam reaching the extraction channel 1019 is adjusted, and the ion beam is sent to a beam transport system connected to the accelerator 100.

In the present embodiment, the positions of the magnetic pole central axis 13 and an ion incident axis 12 are different. A radio frequency kicker 40 is near an outer periphery of the ion circulation space 10. The ion incident axis 12 along the through hole 24 into which ions are incident is located between the magnetic pole central axis 13 and the radio frequency kicker 40. The radio frequency kicker 40 is coupled to the upper magnetic pole 8 and the lower magnetic pole 9 by a support member made of a nonmagnetic insulator, and is supported by the support member.

Figure 3:
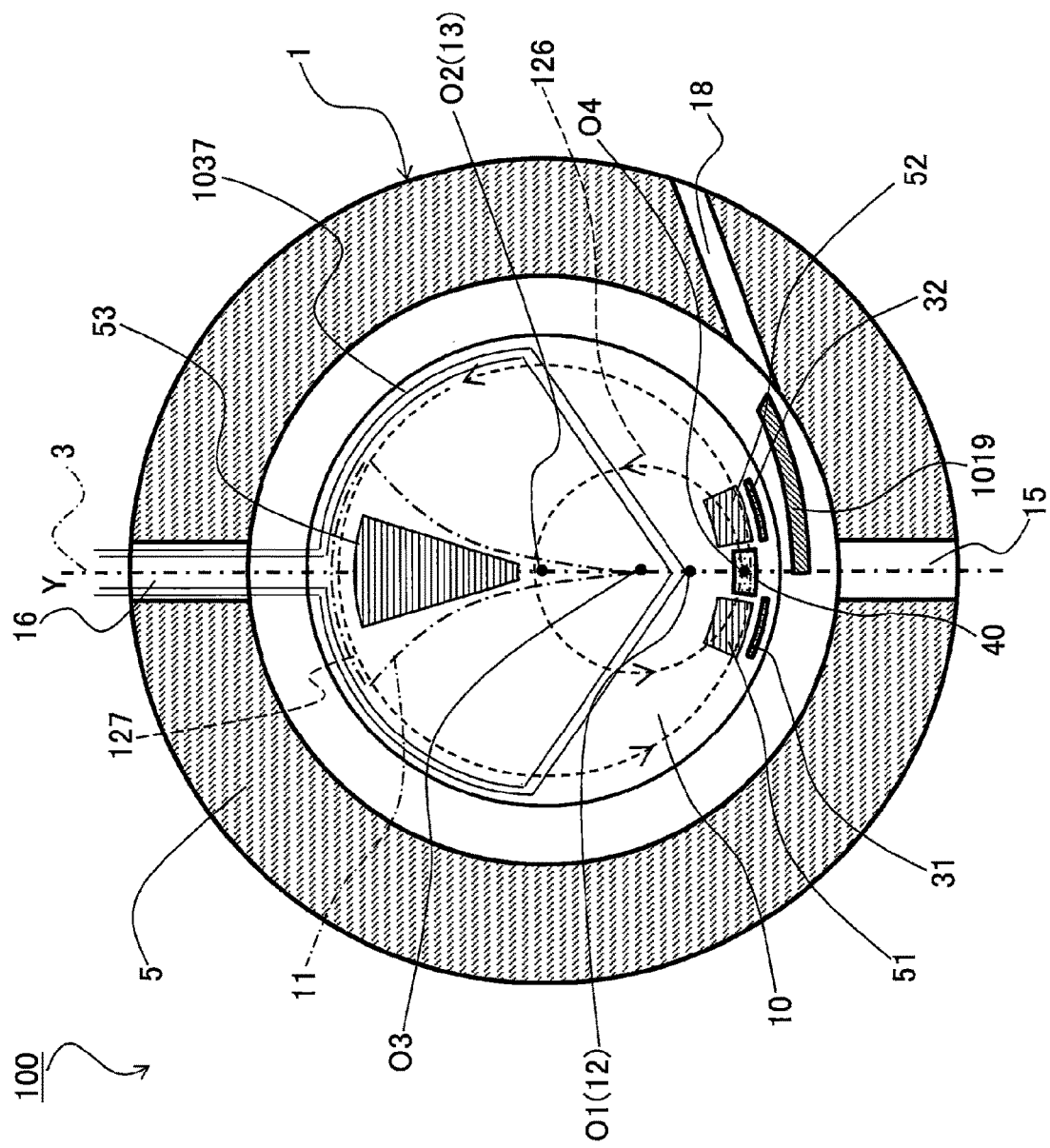
FIG. 3 is a plan view of the accelerator cut along a reference plane and viewed from above.

FIG. 3 is a plan view of the accelerator 100 cut along the reference plane 2 and viewed from above toward the lower return yoke 5. Since the main magnetic field magnet 1 according to the present embodiment has a vertically symmetrical structure with respect to the reference plane 2, the structure on a lower side of the main magnetic field magnet 1 will be described below with reference to FIGS. 2 and 3, and the description of the structure on an upper side of the main magnetic field magnet 1 will be simplified.

In FIG. 3, trajectories 126 and 127 (ion beam trajectories) of ion beams having constant energy are indicated by broken lines. An arrow attached to a broken line indicates a traveling direction of the ion beam. A center point O3 of the ion beam trajectory 126 (Hereinafter, the ion beam trajectory is referred to as a beam trajectory) is deviated from the magnetic pole center axis 13 toward the ion incident axis 12.

A center point of the beam trajectory 127 corresponding to the ion beam having the maximum energy among the extracted ion beams generally coincides with the magnetic pole center axis 13. The beam trajectory 126 corresponding to the ion beam having the minimum energy among the extracted ion beams has the center point O3 on a line segment connecting a magnetic pole center point O2 and an ion incident point O1. Here, the ion incident point O1 is an intersection point between the ion incident axis 12 and the reference plane 2. Furthermore, the magnetic pole center point O2 is an intersection point between the magnetic pole center axis 13 and the reference plane 2, and is a center point of the ion circulation space 10.

A region on an opposite side of the magnetic pole center point O2 as viewed from the ion incident point O1 is an aggregation region in which the beam trajectories are biased and the trajectory interval is narrowed. On the other hand, a side of the magnetic pole center point O2 as viewed from the ion incident point O1 is a discrete region in which the beam trajectories are biased and the trajectory interval is widened. The radio frequency kicker 40 is disposed at an ion extraction operating point O4 in the aggregation region, and the beam trajectory 126 corresponding to low energy and the beam trajectory 127 corresponding to high energy pass through the radio frequency kicker 40.

Here, the ion extraction operating point O4 is a point that causes a physical phenomenon that increases an amplitude of the betatron oscillation. The ion extraction operating point O4 in the present embodiment is a point that is on the opposite side of the magnetic pole center point O2 as viewed from the ion incident point O1 and is on the beam trajectory of the ion reaching the extracted energy. The ion extraction operating point O4 is conceived on each of the beam trajectories of the ion beams having different energies. The ion extraction operating point O4 is on a straight line connecting the magnetic pole center point O2 and the ion incident point O1. At the ion extraction operating point O4, a radio frequency electric field for increasing the amplitude of the betatron oscillation is applied to the ion beam. As a modification, the ion extraction operating point O4 may not necessarily be on the straight line connecting the magnetic pole center point O2 and the ion incident point O1.

Trim coils 51 and 52 are disposed in the vicinity of the radio frequency kicker 40 disposed at the ion extraction operating point O4 with the vertical plane 3 interposed therebetween. Although not illustrated in FIG. 3, a pair of the trim coils 51 vertically faces each other with the reference plane 2 interposed therebetween, and a pair of the trim coils 52 vertically faces each other with the reference plane 2 interposed therebetween. In each of the trim coils 51 and 52, the pair of coils may be disposed to face each other vertically with the reference plane 2 interposed therebetween, or may be disposed only on the upper side or only on the lower side. Furthermore, a pair of trim coils 53 vertically opposed to each other with the reference plane 2 interposed therebetween is disposed in a region on an opposite side of the ion extraction operating point O4 (the position of the radio frequency kicker 40) with the ion incident point O1 interposed therebetween.

A radiofrequency acceleration cavity 1037 has a fan shape covering a part of the beam trajectory in the region on the opposite side of the ion extraction operating point O4 as viewed from the ion incident point O1. The radiofrequency acceleration cavity 1037 is connected to a waveguide tube outside the accelerator 100 through a through hole 16 provided in the side walls of the upper return yoke 4 and the lower return yoke 5. As illustrated in FIG. 2, one of the pair of trim coils 53 is disposed in a space between the radiofrequency acceleration cavity 1037 and the upper magnetic pole 8, and the other of the pair of trim coils 53 is disposed in a space between the radiofrequency acceleration cavity 1037 and the lower magnetic pole 9.

The upper trim coil 53 may be attached to the upper magnetic pole 8. Similarly, the lower trim coil 53 may be attached to the lower magnetic pole 9. The trim coil 53 may be disposed only above the radiofrequency acceleration cavity 1037 and not below the radiofrequency acceleration cavity 1037. Furthermore, the trim coil 53 may be disposed only below the radiofrequency acceleration cavity 1037 and may not be disposed above the radiofrequency acceleration cavity 1037.

In this manner, the trim coil 53 is provided on at least one of a side of the upper magnetic pole 8 and a side of the lower magnetic pole 9 with respect to the reference plane 2 sandwiched between the upper magnetic pole 8 and the lower magnetic pole 9. As described later, the trim coil 53 causes spatial magnetic field variations when the ion circulation space 10 is viewed along the beam trajectory.

In a wide interval region 11 indicated by a one-dot chain line in FIG. 3, the magnetic pole interval, which is a distance between the upper magnetic pole 8 and the lower magnetic pole 9, is larger than that in a peripheral region other than the wide interval region 11. The wide interval region 11 may be, for example, a region that extends in a predetermined azimuth angle range on an opposite side to a side where the radio frequency kicker 40 is disposed when viewed from the center of each of beam trajectories corresponding to different energies. The wide interval region 11 may be provided, for example, over a region occupied by the beam trajectory corresponding to the energy to be extracted. That is, the wide interval region 11 may be provided in the vicinity of an outer periphery of the ion circulation space 10. In the wide interval region 11, the upper magnetic pole 8 may be recessed upward, or the lower magnetic pole 9 may be recessed downward. Furthermore, in the wide interval region 11, both the upper magnetic pole 8 and the lower magnetic pole 9 may be recessed vertically.

A gradient magnetic field magnet 31 (peeler) and a gradient magnetic field magnet 32 (regenerator) are disposed on an outer peripheral side of the radio frequency kicker 40 with the vertical plane 3 interposed therebetween. When viewed from the radio frequency kicker 40, the extraction channel 1019 is disposed on an outer peripheral side across a circumference along which the gradient magnetic field magnet 31 and the gradient magnetic field magnet 32 are disposed. The side walls of the upper return yoke 4 and the lower return yoke 5 are provided with a through hole 18 for installing a beam transport system from which an ion beam is extracted.

A magnetic field distribution generated by the gradient magnetic field magnet 31 may be a distribution in which the magnetic field decreases radially outward. Furthermore, a magnetic field distribution generated by the gradient magnetic field magnet 32 may be a distribution in which the magnetic field increases radially outward.

Note that the gradient magnetic field magnets 31 and 32 may be formed integrally with the lower magnetic pole 9. For example, the gradient magnetic field magnets 31 and 32 may be formed by adding a magnetic body to a surface of the lower magnetic pole 9 or processing a shape of the surface of the lower magnetic pole 9. Furthermore, the gradient magnetic field magnets 31 and 32 may be manufactured as separate members and then engaged with the lower magnetic pole 9 by a method such as welding or bolting.

Furthermore, a magnetic field in a region from the outer peripheries of the upper magnetic pole 8 and the lower magnetic pole 9 to the side walls of the upper return yoke 4 and the lower return yoke 5 decreases radially outward. Therefore, the gradient magnetic field magnet 31 may not be used depending on the degree of reduction in the magnetic field.

Figure 4:
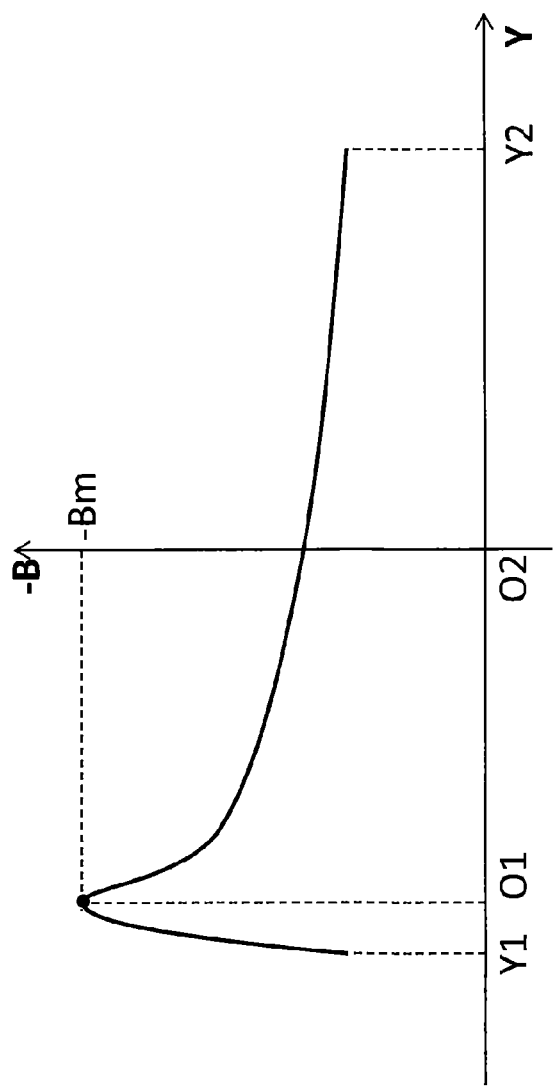
FIG. 4 is a diagram illustrating a distribution of a circumferential magnetic field average value.

FIG. 4 illustrates a distribution of a circumferential magnetic field average value. A horizontal axis indicates a position on an intersection line of the reference plane 2 and the vertical plane 3, and a vertical axis indicates a circumferential magnetic field average value. The circumferential magnetic field average value is an average value of a magnetic field over one circumference in a circumferential direction of the ion circulation space 10. As illustrated in FIG. 4, the circumferential magnetic field average value increases from a position Y1 on the aggregation region toward a side of the discrete region, and the circumferential magnetic field average value becomes the maximum value Bm at the ion incident point O1. Then, the circumferential average magnetic field monotonously decreases from the ion incident point O1 toward a position Y2 on the discrete region. According to a distribution of the circumferential magnetic average value as illustrated in FIG. 4, the beam circling motion is stabilized by the principle of weak focusing.

Figure 5:
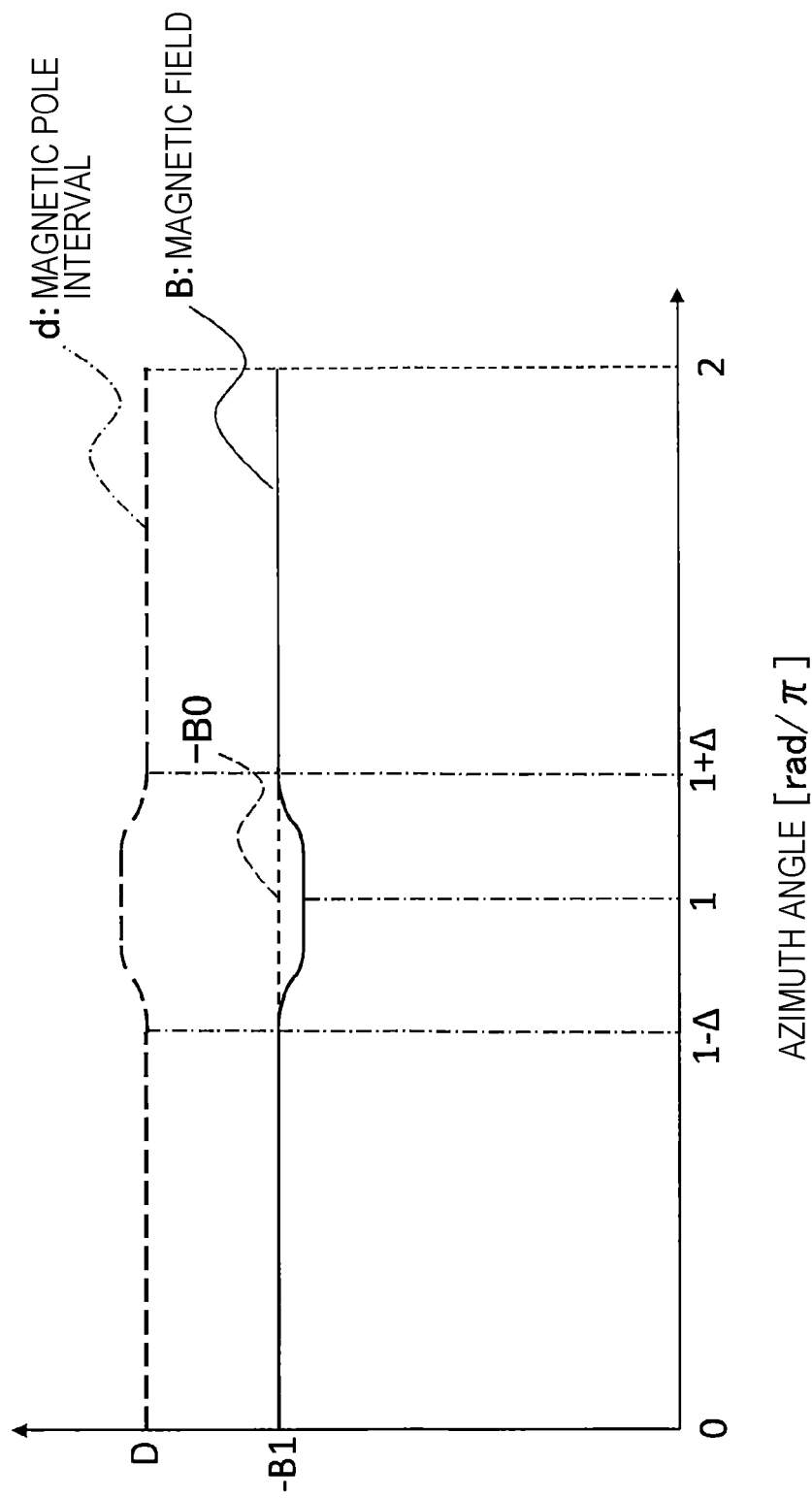
FIG. 5 is a diagram illustrating a circumferential magnetic field distribution and a magnetic pole interval along a beam trajectory.

FIG. 5 illustrates a circumferential magnetic field distribution and a magnetic pole interval along a beam trajectory for an ion beam having constant energy. A horizontal axis indicates a position on a beam trajectory by an azimuth angle, and a vertical axis indicates a magnetic field B and a magnetic pole interval d. The azimuth angle indicates an azimuth when an outside is viewed from a center point of the beam trajectory. The azimuth angle of one turn is normalized by π. An origin at which the azimuth angle is 0 and an end point at which the azimuth angle is 2 correspond to the ion extraction operating point O4. A position where the azimuth angle is 1 corresponds to a position on an opposite side of the ion extraction operating point O4 as viewed from the center point of the beam trajectory.

The magnetic pole interval d is a constant value D when the azimuth angle is in a range of 0 or more and 1−Δ or less and in a range of 1+Δ or more and 2 or less. The ranges of the azimuth angle correspond to a region that is not the wide interval region 11 illustrated in FIG. 3. The magnetic pole interval d is larger than D in a range where the azimuth angle exceeds 1−Δ and is less than 1+Δ. The range of the azimuth angle corresponds to the wide interval region 11 illustrated in FIG. 3. With such a magnetic pole interval d, the magnetic field B has a constant value B1 in the region that is not the wide interval region 11 (the azimuth angle is in the range of 0 of more and 1−Δ or less and the range of 1+Δ or more and 2 or less). Then, the magnetic field B becomes smaller than B1 in the wide interval region 11 (range in which the azimuth angle is more than 1−Δ and less than 1+Δ). In FIG. 5, a magnetic field distribution B0 when the magnetic pole interval d is constant is also indicated by a broken line.

As described above, in the accelerator 100 according to the present embodiment, at least one of the upper magnetic pole 8 and the lower magnetic pole 9 is formed such that the magnetic pole interval between the upper magnetic pole 8 and the lower magnetic pole 9 varies when the ion circulation space 10 is viewed along the beam trajectory. As a result, spatial magnetic field variations when the ion circulation space 10 is viewed along the beam trajectory are given to the ion circulation space 10.

In general, the influence exerted on the ion beam by the variation of the magnetic field is evaluated with respect to the BL product, which is the product of a magnitude of the magnetic field and a distance at which the ion beam feels it. A radial displacement amount indicating the influence of the ion beam due to the variation of the magnetic field is defined as a displacement amount of the ion beam at the ion extraction operating point O4 when the BL product is given by 1 mTm.

Figure 6:
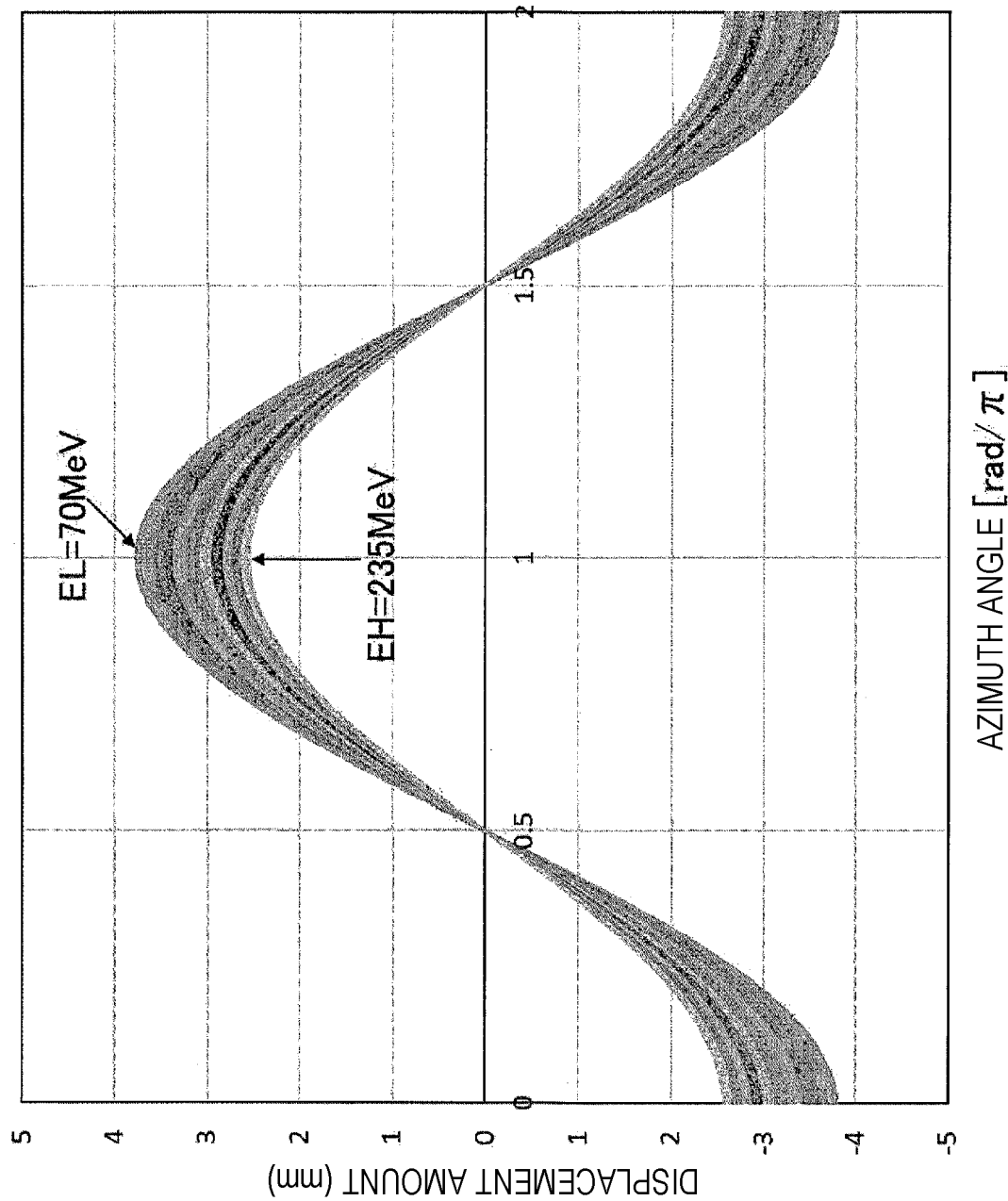
FIG. 6 is a diagram illustrating a displacement amount of a beam trajectory in a radial direction when a constant magnetic field is applied over one circumference of the beam trajectory.

FIG. 6 illustrates an amount of displacement of an ion beam in the radial direction at the ion extraction operating point O4 when the BL product is locally given by 1 mTm on a beam trajectory. In a horizontal axis, a position where the BL product is given to the ion beam is indicated by an azimuth angle measured along a beam progressing direction from the ion extraction operating point O4. A vertical axis indicates an amount of displacement in the radial direction of the ion beam generated at the ion extraction operating point O4, and the radial outside is positive.

In the example illustrated in FIG. 6, when the BL product is given by 1 mTm at the extraction operating point O4, the ion beam of energy EL=70 MeV at the position of the ion extraction operating point O4 is displaced radially inward by about 3.8 mm, and the ion beam of energy EH=235 MeV is displaced radially inward by about 2.6 mm. Then, when the BL product of 1 mTm is given on an opposite side of the ion extraction operating point O4 across a center point of the beam trajectory, the ion beam of energy EL=70 MeV at the extraction operating point O4 is displaced radially outward by about 3.8 mm, and the ion beam of energy EH=235 MeV is displaced radially outward by about 2.6 mm.

As described above, when a part of the magnetic field on the beam trajectory is weakened, that is, when a magnetic field ΔB applied to the original magnetic field is set to be positive, the displacement amount of the ion beam differs according to the energy of the ion beam and the position where the magnetic field is weakened. Specifically, in a case where the magnetic field is weakened in a part in a range where the azimuth angle is 0 or more and 0.5 or less, and in a case where the magnetic field is weakened in a part in a range where the azimuth angle is 1.5 or more and 2 or less, the smaller the energy, the larger the displacement amount toward the inside. Then, in a case where the magnetic field is weakened in a part of a range where the azimuth angle is more than 0.5 and less than 1.5, the smaller the energy, the larger the displacement amount toward the outside.

FIG. 6 illustrates the displacement amount of the ion beam when the magnetic field from the upper magnetic pole 8 toward the lower magnetic pole 9 is locally weakened. Therefore, the displacement amount of the ion beam in a case where the magnetic field from the upper magnetic pole 8 toward the lower magnetic pole 9 is locally strengthened is obtained by reversing the positive and negative polarities of the displacement amount in FIG. 6. That is, when the magnetic field is strengthened at the position of the ion extraction operating point O4, the 70 MeV ion beam is displaced radially outward by about 3.8 mm, and the 235 MeV ion beam is displaced radially outward by about 2.6 mm. When the magnetic field is strengthened on the opposite side of the ion extraction operating point O4 across the center point of the beam trajectory, the 70 MeV ion beam is displaced radially inward by about 3.8 mm, and the 235 MeV ion beam is displaced radially inward by about 2.6 mm.

The range in which the azimuth angle exceeds 0.5 and is less than 1.5 corresponds to a region closer to the center point of the ion circulation space 10 (closer to the magnetic pole center point O2) than to the center point of the beam trajectory. In the following description, a region corresponding to the range in which the azimuth angle exceeds 0.5 and is less than 1.5 is referred to as a first region. Furthermore, the range of the azimuth angle of 0 or more and 0.5 or less and the range of the azimuth angle of 1.5 or more and 2 or less correspond to a region closer to the ion extraction operating point O4 than to the center point of the beam trajectory. In the following description, a region corresponding to the range in which the azimuth angle is 0 or more and 0.5 or less and the range in which the azimuth angle is 1.5 or more and 2 or less is referred to as a second region.

As described above, when the magnetic field is locally weakened in the first region or when the magnetic field is locally strengthened in the second region, the displacement amount toward the outside increases as the energy decreases at the ion extraction operating point O4.

In the present embodiment, by weakening the magnetic field in the first region or strengthening the magnetic field in the second region, the displacement amount toward the outside is increased as the energy of the ion beam is smaller at the position (ion extraction operating point) where the radio frequency kicker 40 is disposed.

That is, an evaluation value of the magnetic pole interval along the beam trajectory in the first region is larger than an evaluation value of the magnetic pole interval along the beam trajectory in the second region. Here, the evaluation value of the magnetic pole interval is a value for evaluating the magnitude of the magnetic pole interval. The larger the overall magnetic pole interval along the beam trajectory is evaluated, the larger the evaluation value is. Furthermore, the evaluation value may be defined as a value at which an outer displacement effect of the ion beam (effect that the low-energy ion beam is displaced outward at the ion extraction operating point) increases as the value for the first region increases. Examples of the evaluation value of the magnetic pole interval along the beam trajectory include statistical values such as an average value, a root mean square, a median value, and a mode of the magnetic pole interval obtained along the beam trajectory.

Such a structure of the upper magnetic pole 8 and the lower magnetic pole 9 causes spatial magnetic field variations when the ion circulation space 10 is viewed along the beam trajectory. The magnetic field variations are spatial magnetic field variations that displace ions such that the amount of displacement in the outward direction at the ion extraction operating point O4 is larger for ions having smaller energy.

The magnetic field evaluation value along the beam trajectory in the first region is smaller than the magnetic field evaluation value along the beam trajectory in the second region. Here, the magnetic field evaluation value is a value for evaluating the magnitude of the magnetic field in the ion circulation space 10. As the magnetic field from the upper magnetic pole 8 toward the lower magnetic pole 9 along the beam trajectory is evaluated to be totally large, the magnetic field evaluation value is larger. Furthermore, the magnetic field evaluation value may be defined as a value at which the outer displacement effect of the ion beam increases as the value for the first region decreases. Examples of the magnetic field evaluation value along the beam trajectory include statistical values such as an average value, a root mean square, a median value, and a mode of the magnetic field obtained along the beam trajectory.

Due to such a structure and magnetic field distribution, the smaller the energy, the larger the displacement amount to the outside of the beam trajectory at the ion extraction operating point O4. As a result, for an ion beam having relatively small energy, the time required for extracting the ion beam is shortened, and the time response characteristic at the time of extracting the ion beam is improved.

Hereinafter, the principle by which the ion beam is extracted from the accelerator 100 will be described based on a physical phenomenon. A displacement amount δ of the ion beam is expressed by the following (Mathematical formula 1).

$$\delta = \frac{\sqrt{\beta(s)\beta(s_0)}}{2\sin\pi\nu}\cos(\pi\nu - |\psi(s) - \psi(s_0)|)$$ [Mathematical formula 1]

Here, β represents a horizontal direction betatron amplitude of the ion beam, ν represents a horizontal direction betatron frequency, s and $s_0$ represent positions on the beam trajectory, and ψ(s)–ψ($s_0$) represent a phase difference of the betatron oscillation. The horizontal direction betatron amplitude β, the beam trajectory, and the phase ψ of the betatron oscillation depend on the energy of the ion beam.

In the present embodiment, a gradient magnetic field by the gradient magnetic field magnets 31 and 32 is applied to the ion beam, and the ion beam is extracted using a resonance in the horizontal direction of the beam called 2/2 resonance. At this time, the horizontal direction betatron oscillation frequency ν may be a value close to 1. When the horizontal direction betatron frequency ν is 1, the phase of the betatron oscillation increases by approximately 2π during one cycle of the ion beam.

In a case where the horizontal direction betatron oscillation frequency ν is 1, the phase difference ψ(s)–ψ($s_0$) is substantially π when s and $s_0$ are substantially shifted by half, and the argument of the cosine function cos is substantially 0. Furthermore, when s and $s_0$ match, the argument of the cosine function cos is substantially π. Correspondingly, in FIG. 6, peaks appear when the azimuth angle is 0 and when the azimuth angle is 1, and the displacement amount of the ion beam is different according to the energy. In a case where the ion beam is extracted using the 2/2 resonance, a radio frequency electric field (disturbance electric field) is generated at a position where the azimuth angle is 0 by a radio frequency electric field generator such as the radio frequency kicker 40 to cause displacement of the ion beam, so that the ion beam is efficiently extracted from the accelerator 100.

A specific operation of the accelerator 100 according to the present embodiment will be described. Ions generated by the ion source 1003 are incident on the reference plane 2 through the through hole 24. The ions are accelerated by the radiofrequency acceleration cavity 1037, circulate while increasing the trajectory radius, and reach the trajectory passing through the radio frequency kicker 40. As the ions circulate while increasing the trajectory radius, the energy of the ions increases.

The radio frequency electromagnetic field excited in the radiofrequency acceleration cavity 1037 at the timing when the energy of the ions reaches the target energy is blocked, and the radio frequency electric field is excited from the radio frequency kicker 40. As a result, the amplitude of the betatron oscillation in the horizontal direction increases, and the ion beam passes through a region where the gradient magnetic field magnet 31 and the gradient magnetic field magnet 32 act, which are located on the radially outer side of the radio frequency kicker 40. Moreover, the 2/2 resonance occurs, the ion beam diverges in the horizontal direction and reaches the extraction channel 1019, and the ion beam is separated from the closed orbit by the extraction channel 1019. The ion beam separated from the closed orbit is extracted to the outside of the accelerator 100 through the through hole 18.

In the present embodiment, the magnetic field is not constant along the beam trajectory, and as illustrated in FIG. 5, the magnetic field is reduced in the wide interval region 11 as compared with the region other than the wide interval region 11. As a result, at the ion extraction operating point O4 at which the radio frequency kicker 40 is disposed, the interval between the beam trajectories of the ion beams having different energies is narrowed.

Therefore, for the ion beam having relatively small energy, the betatron oscillation amplitude necessary for extracting the ion beam becomes small, and the time from the application of the radio frequency voltage to the radio frequency kicker 40 to the extraction of the ion beam becomes short. As a result, the timing at which the ion beam is extracted is controlled with high accuracy.

In the present embodiment, the wide interval region 11 is provided in the ion circulation space 10 sandwiched between the upper magnetic pole 8 and the lower magnetic pole 9. A structure in which the trim coil 53 weakens the magnetic field may be adopted without providing the wide interval region 11 in the accelerator 100.

Furthermore, the embodiment in which the wide interval region 11 is provided in the first region has been described above. In the ion circulation space 10, a narrow interval region may be provided in the second region. The narrow interval region is a region having a smaller magnetic pole interval than the peripheral region.

Second Embodiment

Figure 7:
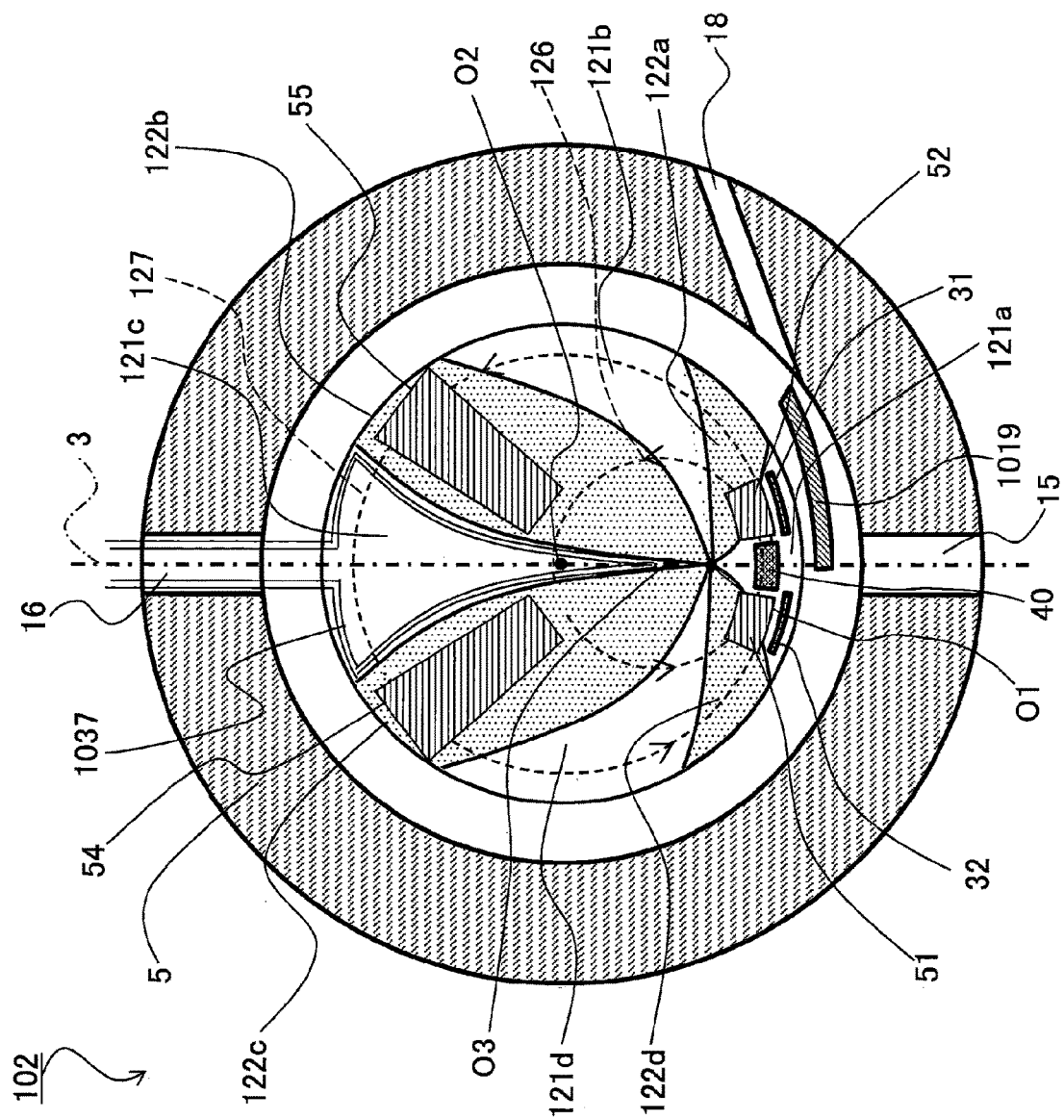
FIG. 7 is a plan view of the accelerator cut along a reference plane and viewed from above.

FIG. 7 illustrates an accelerator 102 according to a second embodiment of the present invention. FIG. 7 is a plan view of the accelerator 102 cut along a reference plane 2 and viewed from above toward a lower return yoke 5. Recesses 121a, 121b, 121c, and 121d are formed in the lower return yoke 5. The recesses 121a, 121b, 121c, and 121d are regions recessed downward. By forming the recesses, protrusions 122a, 122b, 122c, and 122d are formed in the lower return yoke 5. The protrusions 122a, 122b, 122c, and 122d are regions protruding upward with respect to a deepest portion of each recess.

Each recess and each protrusion may be provided over a region occupied by a beam trajectory corresponding to energy to be extracted. That is, each recess and each protrusion may be provided near an outer periphery of an ion circulation space 10.

When the lower return yoke 5 is viewed along the beam trajectory, the recesses and the protrusions are alternately arranged. Also in an upper return yoke 4, recesses are formed in opposing regions above the recesses 121a, 121b, 121c, and 121d formed in the lower return yoke 5. Also in the upper return yoke 4, protrusions are formed in opposing regions above the protrusions 122a, 122b, 122c, and 122d formed in the lower return yoke 5.

The recesses and the protrusions may be provided in any one of the upper return yoke 4 and the lower return yoke 5, or may be provided in both the upper return yoke 4 and the lower return yoke 5.

Furthermore, a region where an extraction channel 1019 is disposed corresponds to the recess of the upper return yoke 4 or the recess of the lower return yoke 5.

As described above, in the accelerator 102 according to the present embodiment, at least one of an upper magnetic pole 8 and a lower magnetic pole 9 is formed such that a magnetic pole interval between the upper magnetic pole 8 and the lower magnetic pole 9 varies when the ion circulation space 10 is viewed along the beam trajectory. As a result, the accelerator 102 according to the present embodiment is configured such that there are spatial magnetic field variations when the ion circulation space 10 is viewed along the beam trajectory. That is, in at least one of the upper magnetic pole 8 and the lower magnetic pole 9, recesses and protrusions are alternately formed along the beam trajectory on a surface facing the ion circulation space 10.

In the following description, a region where the recess belonging to the upper return yoke 4 and the recess belonging to the lower return yoke 5 face each other is referred to as a valley region. Furthermore, a region where the protrusion belonging to the upper return yoke 4 and the protrusion belonging to the lower return yoke 5 face each other is referred to as a hill region. In the valley region, since the magnetic pole interval is larger than that in the hill region, the magnetic field is smaller than that in the hill region.

A radiofrequency acceleration cavity 1037 may be installed in the valley region. In the present embodiment, the radiofrequency acceleration cavity 1037 is installed in a valley region sandwiched between the recess 121c formed in the upper return yoke 4 and the recess 121c formed in the lower return yoke 5. In the present embodiment, a range of an azimuth angle at which the ion beam passes through the radiofrequency acceleration cavity 1037 is narrower than that in the first embodiment. Therefore, in the present embodiment, a frequency of the radio frequency electromagnetic field excited in the radiofrequency acceleration cavity 1037 is higher than that in the first embodiment.

Trim coils 54 and 55 are installed in the hill regions on both sides of the exterior of the radiofrequency acceleration cavity 1037. As a result, the trim coils 54 and 55 approach the reference plane 2 as compared with the case of being installed in the valley region formed by the recesses 121c. Therefore, a magnetomotive force generated from each of the trim coils 54 and 55 for adjusting the beam trajectory is reduced as compared with the case of being installed in the valley region formed by the recesses 121c.

Trim coils 51 and 52 are disposed on the protrusion 122d. Since the trim coils 51 and 52 are disposed in the hill region by the protrusion 122d, the trim coils 51 and 52 approach the reference plane 2 as compared with a case where the trim coils are disposed in the valley region. Therefore, a magnetomotive force generated from each of the trim coils 51 and 52 to adjust the beam trajectory is reduced as compared with the case of being installed in the valley region.

Figure 8:
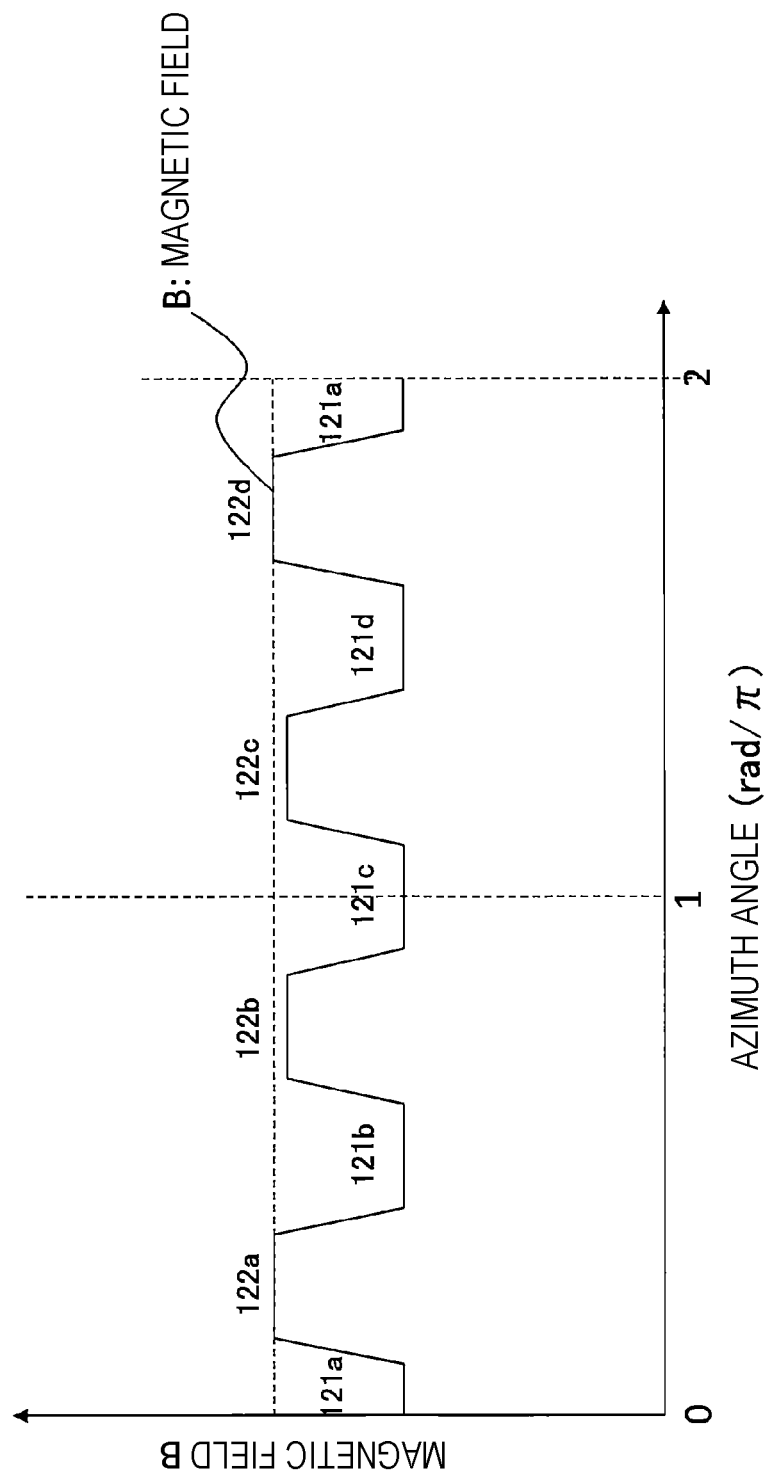
FIG. 8 is a diagram illustrating a distribution of a magnetic field along a beam trajectory.

FIG. 8 illustrates a distribution of a magnetic field along the beam trajectory. A horizontal axis indicates an azimuth angle along the beam trajectory, and a vertical axis indicates the magnetic field B. The distribution of the magnetic field is a magnetic field distribution in a case where the magnetic pole interval of each hill region by the protrusions 122b and 122c is larger than the magnetic pole interval of each hill region by the protrusions 122a and 122d. As a result, the magnetic field in each hill region by the protrusions 122b and 122c is smaller than the magnetic field in each hill region by the protrusions 122a and 122d.

By making the magnetic field in each of the hill regions by the protrusions 122b and 122c smaller than the magnetic field in each of the hill regions by the protrusions 122a and 122d, at a position of the radio frequency kicker 40, an amount of displacement of the beam trajectory to the radial outside increases as the energy decreases. As a result, for the ion beam having relatively small energy, an amplitude of the betatron oscillation required to extract the ion beam becomes small, and the time from the application of a radio frequency voltage to the radio frequency kicker 40 to the extraction of the ion beam becomes short. Therefore, the timing at which the ion beam is extracted is controlled with high accuracy.

In the accelerator 102, the recesses and the protrusions are alternately arranged along the beam trajectory, and the strength of the magnetic field alternately appears when viewed along the beam trajectory. Therefore, the betatron oscillation of the ion beam in the vertical direction is stabilized, and the divergence of the ion beam in the vertical direction is suppressed.

Furthermore, since the extraction channel 1019 is disposed in the valley region, the magnetic field in the extraction channel 1019 is weakened. As a result, the number of ions extracted in the extraction channel 1019 increases under the condition that the magnetomotive force generated by an electromagnet included in the extraction channel 1019 is constant.

Note that, instead of adjusting the magnetic pole interval, a configuration in which the magnetic field is weakened by the trim coil 54 or 55 may be adopted. Furthermore, the embodiment in which the radio frequency kicker 40 is disposed at the ion extraction operating point O4 has been described above. A disturbance magnetic field generator that generates a disturbance magnetic field may be disposed at or near the ion extraction operating point O4. The disturbance magnetic field generator applies a disturbance magnetic field to the ion beam to increase the betatron amplitude in the horizontal direction of the ion beam. The disturbance magnetic field generator may be configured by a plurality of coils as shown in PTL 2.

Figure 9:
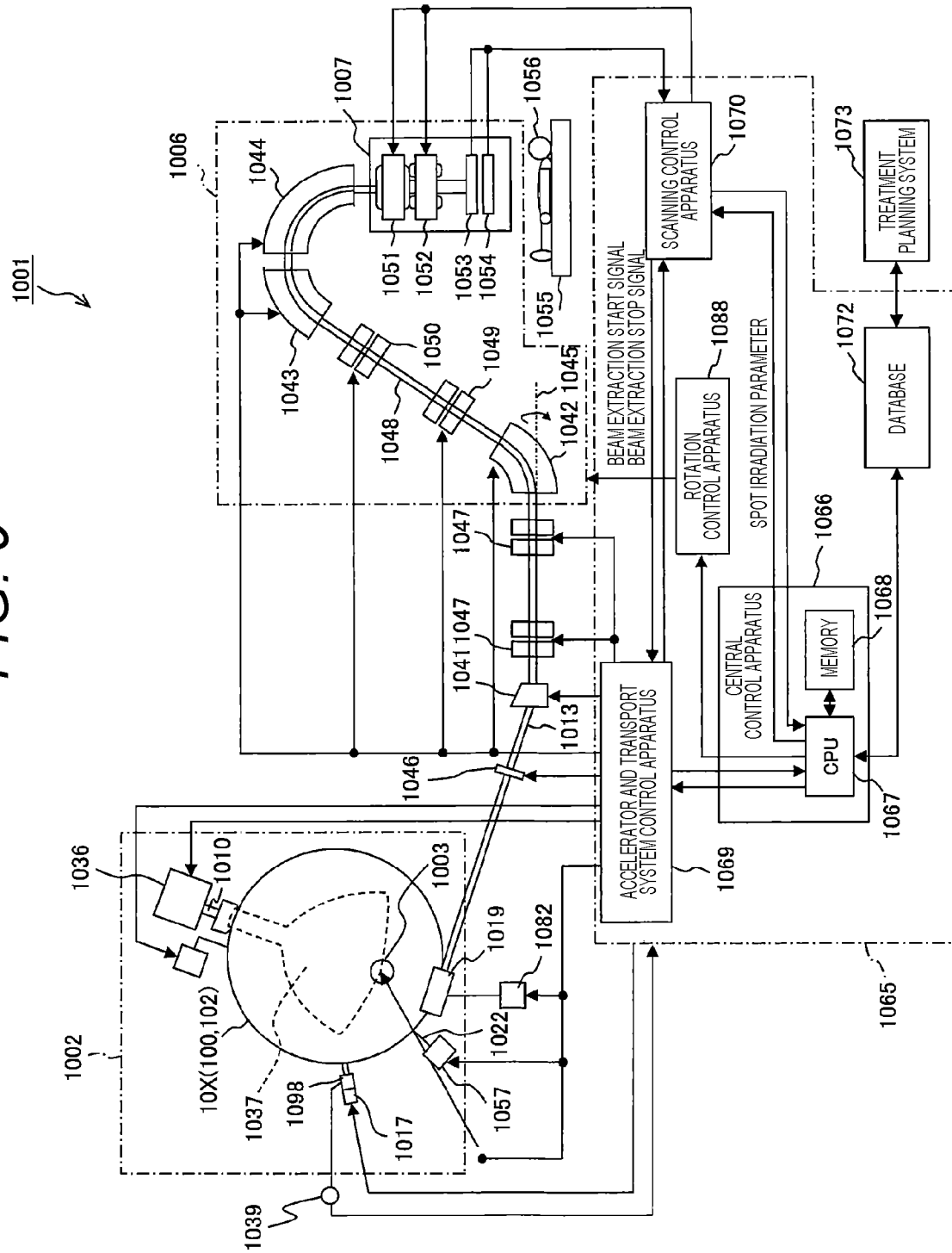
FIG. 9 is a diagram illustrating a configuration of a particle therapy system.

Next, a particle therapy system using the accelerator 100 or 102 according to each of the above embodiments will be described. FIG. 9 illustrates a configuration of a particle therapy system 1001. The particle therapy system 1001 is installed on a floor surface of a building (not illustrated). The particle therapy system 1001 includes an ion beam generator 1002, a beam transport system 1013, a rotating gantry 1006, an irradiation device 1007, and a control system 1065.

The ion beam generator 1002 includes an ion source 1003 and the accelerator 100 or 102 (In the following description, the accelerator 100 or 102 is referred to as accelerator 10X.) to which the ion source 1003 is connected.

A coil excitation power supply 1057 is connected to the coil 6 (FIG. 2) provided in the accelerator 10X via a coil lead wiring 1022. The coil excitation power supply 1057 applies a current to the coil 6.

A radiofrequency power supply 1036 inputs an electromagnetic field into the radiofrequency acceleration cavity 1037 installed in the accelerator 10X through a waveguide 1010, and excites a radio frequency electric field that accelerates an ion beam between an electrode connected to the radiofrequency acceleration cavity 1037 and a ground electrode. In the accelerator 10X, a resonance frequency of the electromagnetic field excited in the radiofrequency acceleration cavity 1037 is modulated corresponding to the energy of the ion beam. In order to modulate the frequency, inductance or electrostatic capacitance may be adjusted. A known method may be used as a method of adjusting the inductance or the electrostatic capacitance. For example, in the case of adjusting the electrostatic capacitance, a variable capacitance capacitor is connected to the radio frequency cavity, and the electrostatic capacitance of the variable capacitance capacitor is controlled.

A power supply 1082 for the extraction channel is connected to an electromagnet included in the extraction channel 1019. By causing a current to flow from the power supply 1082 for the extraction channel to the electromagnet provided in the extraction channel 1019, the ion beam reaching the extraction channel 1019 is adjusted, and the ion beam is sent to the beam transport system 1013. A beam current measurement device 1098 includes a mobile device 1017 and a position detector 1039.

The beam transport system 1013 has a beam path 1048 that reaches the irradiation device 1007. The beam transport system 1013 further includes a plurality of quadrupole magnets 1046, a bending magnet 1041, a plurality of quadrupole magnets 1047, a bending magnet 1042, quadrupole magnets 1049 and 1050, and bending magnets 1043 and 1044.

In the beam path 1048, the plurality of quadrupole magnets 1046, the bending magnet 1041, the plurality of quadrupole magnets 1047, the bending magnet 1042, the quadrupole magnets 1049 and 1050, and the bending magnets 1043 and 1044 are arranged in this order from the accelerator 10X toward the irradiation device 1007.

A part of the beam path 1048 included in the beam transport system 1013 is provided in the rotating gantry 1006. The bending magnet 1042, the quadrupole magnets 1049 and 1050, and the bending magnets 1043 and 1044 included in the beam transport system 1013 are also provided in the rotating gantry 1006. The beam path 1048 is connected to the extraction channel 1019 provided in the accelerator 10X.

The rotating gantry 1006 is configured to be rotatable about a rotation shaft 1045, and is a rotation device that rotates the irradiation device 1007 about the rotation shaft 1045.

The irradiation device 1007 includes two scanning magnets 1051 and 1052, a beam position monitor 1053, and a dose monitor 1054. The scanning magnets 1051 and 1052, the beam position monitor 1053, and the dose monitor 1054 are arranged along a center axis of the irradiation device 1007, that is, a beam axis. The scanning magnets 1051 and 1052, the beam position monitor 1053, and the dose monitor 1054 are disposed in a casing (not illustrated) of the irradiation device 1007.

The beam position monitor 1053 and the dose monitor 1054 are disposed downstream of the scanning magnets 1051 and 1052. The scanning magnet 1051 and the scanning magnet 1052 deflect the ion beam, and scan the ion beam in directions orthogonal to each other in a plane vertical to the central axis of the irradiation device 1007. The beam position monitor 1053 measures a passing position of the irradiated ion beam. The dose monitor 1054 measures the dose of the irradiated ion beam.

The irradiation device 1007 is attached to the rotating gantry 1006 and is disposed downstream of the bending magnet 1044.

On a downstream side of the irradiation device 1007, a treatment table 1055 on which a patient 1056 lies is disposed so as to face the irradiation device 1007.

The control system 1065 includes a central control apparatus 1066, an accelerator and transport system control apparatus 1069, a scanning control apparatus 1070, a rotation control apparatus 1088, and a database 1072. The central control apparatus 1066 includes a central processing unit (CPU) 1067 and a memory 1068 connected to the CPU 1067. The accelerator and transport system control apparatus 1069, the scanning control apparatus 1070, the rotation control apparatus 1088, and the database 1072 are connected to the CPU 1067 in the central control apparatus 1066.

The particle therapy system 1001 further includes a treatment planning system 1073, and the treatment planning system 1073 is connected to the database 1072. In the particle therapy system 1001, information indicating irradiation energy, an irradiation angle, and the like of a particle beam is created as a treatment planning by the treatment planning system 1073 prior to the irradiation of the particle beam, and the irradiation is executed based on the treatment planning.

The CPU 1067 of the central control apparatus 1066 reads various operation control programs related to irradiation of each device constituting the particle therapy system 1001 from the treatment planning stored in the database 1072. The CPU 1067 of the central control apparatus 1066 executes the read programs and outputs a command via the accelerator and transport system control apparatus 1069, the scanning control apparatus 1070, and the rotation control apparatus 1088, thereby controlling the operation of each device in the particle therapy system 1001.

Note that the programs for executing the control processing may be integrated into one program, each program may be divided into a plurality of programs, or may be a combination thereof. Furthermore, a part or all of the programs may be realized by dedicated hardware or may be modularized. Moreover, the various programs may be installed in each computer by a program distribution server or an external storage medium.

Furthermore, each control apparatus may be an independent device connected by a wired or wireless network, or two or more control apparatuses may be integrated.

With such a configuration, in the particle therapy system 1001, the ions incident on the accelerator 10X from the ion source 1003 are accelerated by the accelerator 10X. The ion beam extracted from the accelerator 10X is transported to the irradiation device 1007 by the beam transport system 1013. The irradiation device 1007 irradiates a target volume of the patient 1056 with the ion beam.

REFERENCE SIGNS LIST

1 main magnetic field magnet
2 reference plane
3 vertical plane
4 upper return yoke
5 lower return yoke
6 coil
7 vacuum container
8 upper magnetic pole
9 lower magnetic pole
10 ion circulation space
11 wide interval region
12 ion incident axis
13 magnetic pole center axis
15, 16, 18, 24 through hole
31, 32 gradient magnetic field magnet
40 radio frequency kicker
51, 52, 53, 54, 55 trim coil
121a, 121b, 121c, 121d recess
122a, 122b, 122c, 122d protrusion
126, 127 beam trajectory
100, 102, 10X accelerator
1001 particle therapy system
1002 ion beam generator
1003 ion source
1006 rotating gantry
1007 irradiation device
1010 waveguide
1017 mobile device
1019 extraction channel
1022 coil lead wiring
1036 radiofrequency power supply
1037 radiofrequency acceleration cavity
1039 position detector
1041 to 1044 bending magnet
1045 rotation shaft
1046, 1047, 1049, 1050 quadrupole magnet
1048 beam path
1051, 1052 scanning magnet
1053 position monitor
1054 dose monitor
1055 treatment table
1056 patient
1057 coil excitation power supply
1065 control system
1066 central control apparatus
1067 CPU
1068 memory
1069 accelerator and transport system control apparatus
1070 scanning control apparatus
1072 database
1073 treatment planning system
1082 power supply for extraction channel
1088 rotation control apparatus
1098 beam current measurement device

The invention claimed is:

1. An accelerator comprising
an upper magnetic pole and a lower magnetic pole sandwiching an ion circulation space in which ions circulate,
wherein the accelerator is configured such that there are spatial magnetic field variations when the ion circulation space is viewed along an ion beam trajectory, and
the magnetic field variations are spatial magnetic field variations that displace ions such that an amount of displacement in an outward direction at an ion extraction operating point is larger for ions having smaller energy.

2. The accelerator according to claim 1, further comprising a trim coil provided on at least one of a side of the upper magnetic pole and a side of the lower magnetic pole with respect to a reference plane sandwiched between the upper magnetic pole and the lower magnetic pole, the trim coil applying the magnetic field variations.

3. The accelerator according to claim 1, further comprising a radio frequency electric field generator disposed at the ion extraction operating point.

4. The accelerator according to claim 1, further comprising a disturbance magnetic field generator disposed at the ion extraction operating point.

5. A particle therapy system comprising:
the accelerator according to claim 1;
a beam transport system that transports the ions extracted from the accelerator; and
an irradiation device that irradiates a patient with the ions transported by the beam transport system.

6. An accelerator comprising
an upper magnetic pole and a lower magnetic pole sandwiching an ion circulation space in which ions circulate,
wherein the accelerator is configured such that there are spatial magnetic field variations when the ion circulation space is viewed along an ion beam trajectory, and
a magnetic field evaluation value along the ion beam trajectory in a region closer to a center point of the ion circulation space than to a center point of the ion beam trajectory is smaller than a magnetic field evaluation value along the ion beam trajectory in a region closer to an ion extraction operating point than to the center point of the ion beam trajectory.

7. An accelerator comprising
an upper magnetic pole and a lower magnetic pole sandwiching an ion circulation space in which ions circulate,
wherein at least one of the upper magnetic pole and the lower magnetic pole is formed such that a magnetic pole interval between the upper magnetic pole and the lower magnetic pole varies when the ion circulation space is viewed along an ion beam trajectory.

8. The accelerator according to claim 7, wherein an evaluation value of the magnetic pole interval along the ion beam trajectory in a region closer to a center point of the ion circulation space than to a center point of the ion beam trajectory is larger than an evaluation value of the magnetic pole interval along the ion beam trajectory in a region closer to an ion extraction operating point than to the center point of the ion beam trajectory.

9. The accelerator according to claim 7, wherein a wide interval region having the magnetic pole interval larger than the magnetic pole interval of a peripheral region is formed in a region closer to a center point of the ion circulation space than to a center point of the ion beam trajectory.

10. The accelerator according to claim 7, wherein a narrow interval region having the magnetic pole interval smaller than the magnetic pole interval of a peripheral region is formed in a region closer to an ion extraction operating point than to a center point of the ion beam trajectory.

11. The accelerator according to claim 7, wherein
in at least one of the upper magnetic pole and the lower magnetic pole,
a recess and a protrusion are alternately formed along the ion beam trajectory on a surface facing the ion circulation space.

12. The accelerator according to claim 11, further comprising a trim coil provided on at least one of a side of the upper magnetic pole and a side of the lower magnetic pole with respect to a reference plane sandwiched between the upper magnetic pole and the lower magnetic pole, the trim coil being provided at a position corresponding to the protrusion.

13. The accelerator according to claim 11, further comprising a radiofrequency acceleration cavity at a position corresponding to the recess formed in at least one of the upper magnetic pole and the lower magnetic pole.

14. The accelerator according to claim 11, further comprising an extraction channel that extracts an ion beam by an electromagnet at a position corresponding to the recess formed in at least one of the upper magnetic pole and the lower magnetic pole.

* * * * *